(12) United States Patent  
Trieu

(10) Patent No.: US 7,857,856 B2
(45) Date of Patent: Dec. 28, 2010

(54) COMPOSITE SPINAL NUCLEUS IMPLANT WITH WATER ABSORPTION AND SWELLING CAPABILITIES

(75) Inventor: Hai H. Trieu, Cordova, TN (US)

(73) Assignee: Warsaw Ortho Pedic, Inc.

( * ) Notice: Subject to any disclaimer, the term of this patent is extended or adjusted under 35 U.S.C. 154(b) by 411 days.

(21) Appl. No.: 11/079,773

(22) Filed: Mar. 15, 2005

(65) Prior Publication Data

US 2006/0210594 A1 Sep. 21, 2006

(51) Int. Cl.
*A61F 2/44* (2006.01)
(52) U.S. Cl. .................................................. 623/17.16
(58) Field of Classification Search ............... 623/17.11, 623/17.12, 17.16
See application file for complete search history.

(56) References Cited

U.S. PATENT DOCUMENTS

| | | | | |
|---|---|---|---|---|
| 3,220,960 A * | 11/1965 | Lim et al. | .................... | 521/149 |
| 4,279,795 A * | 7/1981 | Yamashita et al. | .......... | 523/112 |
| 4,696,974 A | 9/1987 | Suic et al. | | |
| 4,771,089 A * | 9/1988 | Ofstead | ....................... | 524/41 |
| 4,985,253 A | 1/1991 | Fujioka et al. | | |
| 5,047,055 A | 9/1991 | Bao et al. | | |
| 5,192,326 A | 3/1993 | Bao et al. | | |
| 5,324,816 A * | 6/1994 | Khanna et al. | ............... | 528/481 |
| 5,458,643 A * | 10/1995 | Oka et al. | ................. | 623/17.16 |
| 5,556,429 A | 9/1996 | Felt | | |
| 5,976,186 A | 11/1999 | Bao et al. | | |
| 6,063,061 A * | 5/2000 | Wallace et al. | ............... | 604/181 |
| 6,187,048 B1 | 2/2001 | Milner et al. | | |
| 6,264,695 B1 | 7/2001 | Stoy | | |
| 6,280,475 B1 * | 8/2001 | Bao et al. | ................. | 623/17.16 |
| 6,306,177 B1 | 10/2001 | Felt et al. | | |
| 6,552,103 B1 * | 4/2003 | Bertozzi et al. | ............. | 523/106 |
| 6,620,196 B1 | 9/2003 | Trieu | | |
| 6,660,827 B2 | 12/2003 | Loomis et al. | | |
| 6,726,721 B2 | 4/2004 | Stoy et al. | | |
| 6,764,514 B1 * | 7/2004 | Li et al. | .................... | 623/17.12 |
| 2002/0187288 A1 | 12/2002 | Lim et al. | | |
| 2005/0267583 A1* | 12/2005 | Higham et al. | ........... | 623/17.16 |
| 2006/0093648 A1* | 5/2006 | Coury et al. | ................. | 424/426 |

FOREIGN PATENT DOCUMENTS

| | | |
|---|---|---|
| EP | 0 326 278 A1 | 8/1989 |
| EP | 0 399 518 A1 | 11/1990 |
| EP | 0 700 671 A1 | 3/1996 |
| WO | WO 02/17824 A2 | 3/2002 |

* cited by examiner

*Primary Examiner*—Thomas C Barrett
*Assistant Examiner*—Nicholas Woodall

(57) ABSTRACT

Embodiments relate to a spinal nucleus implant with water absorption and swelling capabilities, compositions for producing the spinal nucleus implants, and methods of preparing and using the spinal nucleus implants. The spinal nucleus implant can be created from a composition comprising a mixture of non-hydrogel polymer material and at least one hydrophilic polymer, the weight ratio of non-hydrogel polymer material to the at least one hydrophilic polymer being from about 1:1 to about 19:1.

16 Claims, 4 Drawing Sheets

COMPOSITE SPINAL NUCLEUS IMPLANT WITH WATER ABSORPTION AND SWELLING CAPABILITIES

FIELD OF THE INVENTION

The embodiments relate to a spinal nucleus implant with water absorption and swelling capabilities. The spinal nucleus implant includes a composition comprising a blend of non-hydrogel polymer material and at least one hydrophilic polymer. The weight ratio of non-hydrogel polymer material to the at least one hydrophilic polymer preferably is from about 1:1 to about 19:1. The spinal nucleus implants are useful in treating diseases and/or disorders, such as herniated discs. The spinal nucleus implants optionally may contain polyelectrolytes and elastomer compounds, as well as pharmacological and biological agents.

BACKGROUND OF THE INVENTION

The human spine includes intervertebral discs that are located between adjacent vertebrae of the spine. The intervertebral discs function to stabilize the spine and distribute forces between vertebrae. Intervertebral discs comprise three regions, known as the annulus fibrosis, the nucleus pulposus, and the cartilagenous end plates.

The nucleus pulposus retains a gelatinous consistency, and includes a high proteoglycan content. The nucleus pulposus further retains approximately 70% to 90% water, aiding in its fluid nature. The nucleus pulposus is contained within the annulus fibrosis. The annulus fibrosis retains a more rigid consistency, and is composed primarily of type I and type II collagen. The annulus fibrosis functions to provide peripheral mechanical support to the intervertebral discs, torsional resistance, and resistance to the hydrostatic pressures of the nucleus pulposus.

Intervertebral discs may be displaced or damaged due to trauma or disease. Disruption of the annulus fibrosis may allow the nucleus pulposus to protrude into the vertebral canal, a condition commonly referred to as a herniated or ruptured disc. The extruded nucleus pulposus may press on a spinal nerve, resulting in nerve damage, pain, numbness, muscle weakness and paralysis. Intervertebral discs also may deteriorate due to the normal aging process. As a disc dehydrates and hardens, the disc space height will be reduced, leading to instability of the spine, decreased mobility, and pain.

One way to relieve the symptoms of these conditions is by surgical removal of a portion or all of the intervertebral disc. The removal of the damaged or unhealthy disc may allow the disc space to collapse, which would lead to instability of the spine, abnormal joint mechanics, nerve damage, as well as severe pain. Therefore, after removal of the disc, adjacent vertebrae are sometimes fused to preserve the disc space. Spinal fusion involves inflexibly connecting adjacent vertebrae through the use of bone grafts or mechanical devices. Because the fused adjacent vertebrae are prevented from moving relative to one another, the vertebrae no longer contact each other in the area of the damaged intervertebral disc and the likelihood of continued irritation is reduced. Spinal fusion, however, is disadvantageous because it restricts the patient's mobility by reducing the spine's flexibility.

Attempts to overcome these problems have led researchers to investigate the efficacy of implanting an artificial device to replace the damaged portion of the patient's intervertebral disc. One such prosthesis is an artificial implantable nucleus replacement device. Nucleus implants are used when the nucleus pulposus of the intervertebral disc is damaged but the annulus fibrosis and vertebral end-plates are still sufficiently healthy to retain. Nucleus replacement surgery involves removing the damaged nucleus pulposus of the intervertebral disc and insertion of the nucleus implant inside of the retained annulus fibrosis. The nucleus implant is often a molded polymer device designed to absorb the compressive forces placed on the spine. For increased strength, the nucleus implant may be combined with an internal matrix of, for example, biocompatible fibers. The retained annulus fibrosis provides tensile strength. Some desirable attributes of a hypothetical implantable nucleus replacement device include axially compressibility for shock absorbance, excellent durability to avoid future replacement, and bio-compatibility.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY

There remains a need in the art for synthetic compositions useful in forming nucleus pulposus replacement devices to alleviate injury due to failure of an intervertebral disc. It therefore is a feature of an embodiment of the invention to provide a nucleus implant that has improved water absorption and swelling capabilities upon insertion into a disc space.

In accordance with these and other features of embodiments of the invention, there is provided a spinal nucleus implant composition comprising a non-hydrogel polymer material and at least one hydrophilic polymer, wherein the non-hydrogel polymer material and the at least one hydrophilic polymer are present in a weight ratio from about 1:1 to about 19:1.

In accordance with another feature of an embodiment of the invention, there is provided a method of making a spinal nucleus implant by mixing a non-hydrogel polymer material and at least one hydrophilic polymer in a weight ratio from about 1:1 to about 19:1, molding the mixture into a nucleus implant, and solidifying or curing the non-hydrogel polymer to form the spinal nucleus implant.

In accordance with yet another feature of an embodiment of the invention, there is provided a method of treating or preventing a disease or disorder comprising surgically evacuating at least a portion of the native nucleus pulposus material and any free disc fragments from a disc space. The method also includes producing a spinal nucleus implant as described above, and then inserting the spinal nucleus implant into the at least partially evacuated disc space.

These and other features of the invention will be readily apparent from the detailed description that follows.

DETAILED DESCRIPTION OF PREFERRED EMBODIMENTS

Figure 1:
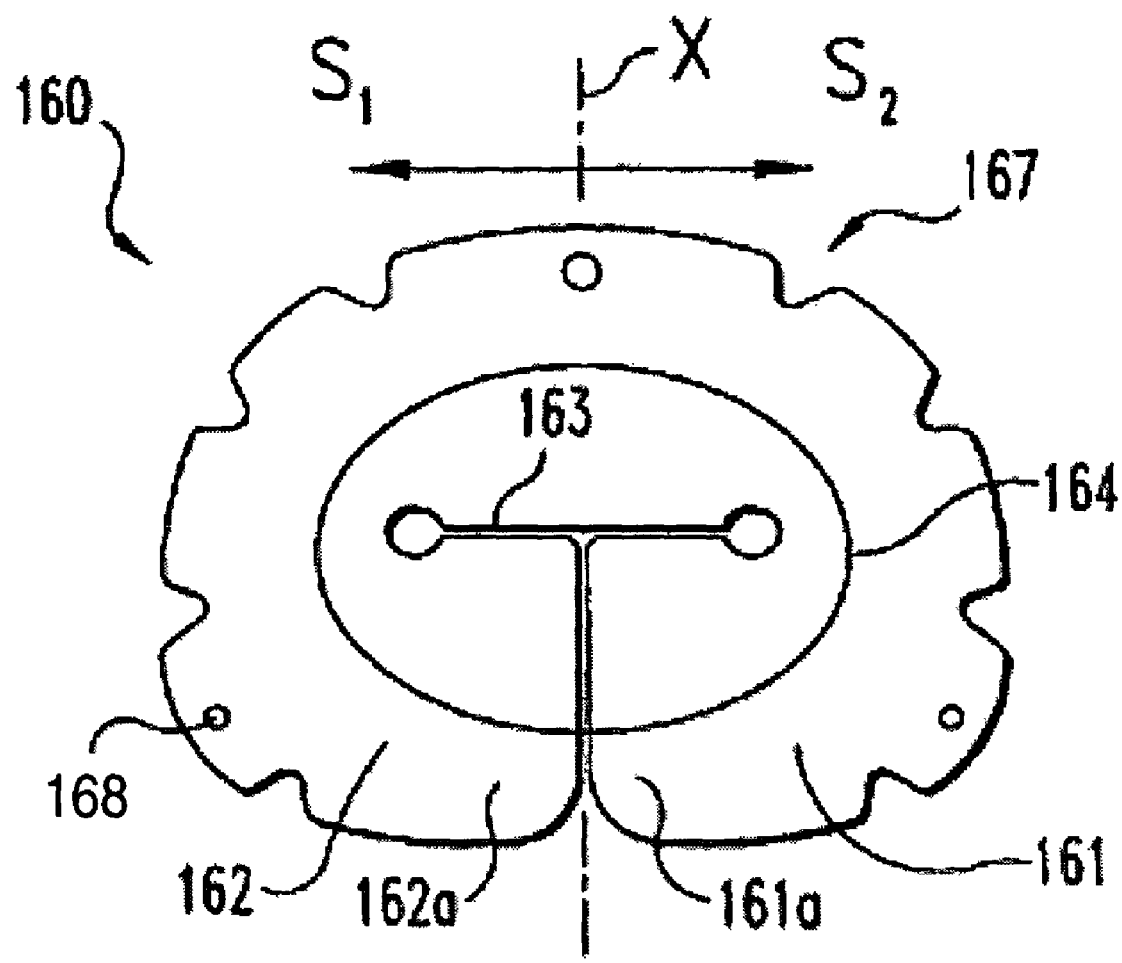
FIG. 1 shows one preferred embodiment of a spinal nucleus implant that may be implanted according to one aspect of the present invention.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a spinal implant" includes a plurality of such implants, as well as a single implant, and a reference to "a therapeutic agent" is a reference to one or more therapeutic and/or pharmaceutical agents and equivalents thereof known to those skilled in the art, and so forth.

As used throughout this description, the term "hydrophilic" denotes a material or substance having an affinity for water. The expression "non-hydrogel polymer material" denotes any polymer composition that is capable of forming a substantially solid mass, and that is not comprised of a hydrogel polymer. Throughout this description, the term "hydrogel" denotes a polymeric material that is capable of absorbing water up to and including its equilibrium water content. Hydrogels include conventional hydrogel materials, as well as xerogel materials, including those disclosed in, for example, U.S. Pat. Nos. 5,047,055, 5,192,326, 5,976,186, 6,264,695, 6,660,827, and 6,726,721, the disclosures of each of which are incorporated by reference herein in their entirety.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the various spinal implants, therapeutic and/or pharmaceutical agents, and other components that are reported in the publications and that might be used in connection with the invention. Nothing herein is to be construed as an admission that the invention is not entitled to antedate such disclosures by virtue of prior invention.

Spinal nucleus implants of the embodiments preferably are produced from polymer compositions comprising a mixture or blend of polymers. Throughout this description, the terms "mixture" and "blend" will be used interchangeably. The polymer composition comprises, or alternatively consists of, a ratio of a non-hydrogel polymer material, and at least one hydrophilic polymer. These polymer compositions can be homogeneous or heterogeneous mixtures or blends, or combinations thereof. For composite homogenous blends, the compositions may vary from interpenetrating network polymers to uniform dispersion of fine particles of the minor component within the major component. For heterogeneous blends, the minor component may exist in course particle form (e.g. 200 microns or larger particles).

The spinal nucleus implant may have either a uniform or a non-uniform composition. By "uniform," it is meant that the ratio of non-hydrogel polymer material to the at least one hydrophilic polymer material is substantially constant throughout the spinal nucleus implant. By "non-uniform," it is meant that the ratio of non-hydrogel polymer material to the at least one hydrophilic polymer material is not substantially constant throughout the spinal nucleus implant. For example, the ratio of hydrophilic polymer to non-hydrogel polymer material in a non-uniform composition may vary by about 10% to about 300% throughout the spinal nucleus implant. A non-uniform spinal nucleus implant may be advantageous to create areas of increased swelling in the spinal nucleus implant. For example, the ratio of non-hydrogel polymer material to hydrophilic polymer may vary from the interior to the exterior of the implant. In another example, the anterior side of the spinal nucleus implant may have a higher percentage of hydrophilic polymer material than the posterior side. This may cause the anterior side of the spinal nucleus implant to swell to a greater height than the posterior side. Alternatively, the posterior side of the spinal nucleus implant may have a higher percentage of hydrophilic polymer material than the anterior side, thereby causing the posterior side to swell to a greater height than the anterior side. Both of these exemplary embodiments may lead to a spinal nucleus implant with a tapered cross section that may be useful to mimic the native intervertebral disc and the natural curvature of the spine. In a preferred embodiment, the ratio of non-hydrogel polymer material to hydrophilic polymer in the posterior side of the implant is in the range of from about 19:1 to about 10:1 and the ratio in the anterior side of the implant is in the range of from about 10:1 to about 1:1.

In one embodiment of the invention, the polymer blend composition comprises, or alternatively consists of, a weight ratio of non-hydrogel polymer material to at least one hydrophilic polymer of from about 1:1 to about 19:1. In a preferred embodiment of the invention, the non-hydrogel polymer material and the at least one hydrophilic polymer exist as a blend in a weight ratio from about 3:1 to about 9:1, and even more preferably in a weight ratio from about 4.5:1 to about 7:1.

Without intending on being bound by any theory of operation, it is believed that the ratio of the hydrophilic polymer(s) described herein to the non-hydrogel polymer material enables the resulting blend to absorb significant amounts of water, once the polymer is placed in a hydrated environment such as the human body. The absorption of water results in swelling of the composite material, and an increase in the mechanical properties of the composite, an increase in the durability and an increase in the biostability of the composition. The non-hydrogel polymer material is believed to provide structural support for the spinal nucleus implant. The non-hydrogel polymer material component of the spinal nucleus implant is believed to prevent unwanted deformation, cracks, tears, breakage or other damage. However, an implant that is completely non-deformable or inflexible may be difficult to implant. Therefore, the ratio of non-hydrogel polymer material to hydrophilic polymer(s) may be chosen in order to yield semi-flexible implants, such as the implant shown in FIGS. 1-5, which may aid in delivery of the device to the implantation site. In a preferred embodiment, the implant may be substantially flexible in the plane perpendicular to the spine column in order to aid in delivery of the device but substantially less flexible in the direction parallel to the spinal column so as to provide adequate support of the spinal column's vertical stresses.

Any non-hydrogel polymer material can be used to form the implant compositions of the invention. Suitable non-hydrogel polymer materials include silicone, polyurethanes, silicone polyurethane copolymers, polyolefins, thermoplastic elastomers, thermoset elastomers, thermoplastic polymers, thermoset polymers, and combinations thereof, such as copolymers. Suitable polyolefins include polyisobutylene rubber and polyisoprene rubber, neoprene rubber, nitrile rubber, vulcanized rubber, and combinations thereof. The vulcanized rubber described herein may be produced, for example, by a vulcanization process utilizing a copolymer produced as described, for example, in U.S. Pat. No. 5,245,098 from 1-hexene and 5-methyl-1,4-hexadiene.

Suitable olefin polymers also include polymers made from ethylenically unsaturated monomers. Olefin polymers typically require a polymerization catalyst to form the polymer, and polymers derived from ethylenically unsaturated monomers typically require a light or heat activated catalyst to polymerize the polymer. Thermoplastic silicone polyurethane copolymers are particularly preferred non-hydrogel polymers for use in the invention.

Non-limiting examples of thermoplastic silicone polyurethane copolymers useful as the non-hydrogel polymer material include, but are not limited to, polyether silicone polyurethanes; polycarbonate silicone polyurethanes; poly(tetramethylene-oxide) (PTMO) polyether-based aromatic silicone polyurethanes; polydimethylsiloxane (PDMS) polyether-based aromatic silicone polyurethanes; PTMO polyether-based aliphatic silicone polyurethanes; PDMS polyether-based aliphatic silicone polyurethanes; silicone polyurethane ureas; and combinations thereof. Suitable thermoplastic silicone polyurethane copolymers are also commercially available, and non-limiting commercially available, suitable thermoplastic silicone polyurethane copolymers comprise, or alternatively consist of, PurSil (including PurSil-10,-20, and -40) (Polymertech, Berkley, Calif.), CarboSil (including CarboSil-10,-20, and -40) (Polymertech, Berkley, Calif.), Elast-Eon silicone polyurethanes with silicone content between 10% and 50% (Aortech Biomaterials, Victoria, Australia), and combinations thereof. Thermoplastic silicone polyurethane copolymers used in the generation of spinal nucleus implants are non-biodegradable.

Hydrophilic polymers useful in forming the spinal nucleus implant of embodiments of the invention include any now known or later discovered hydrophilic polymers. Non-limiting examples of hydrophilic polymers include, but are not limited to, polyacrylamide; polyacrylic acid; polyvinylpyrrolidone; copolymers of ethyleneoxide and propyleneoxide or hyaluronic acid; naturally-occurring materials such as collagen, gelatin, albumin, keratin, elastin, silk, hyaluronic acid and derivatives thereof, proteoglycan, glucomannan gel, and polysaccharides such as cross-linked carboxyl-containing polysaccharides; and combinations thereof.

Hydrophilic polymers optionally may also comprise, or alternatively consist of, one or more hydrogels or xerogels. Suitable hydrogels include natural hydrogels, and those formed from polyvinyl alcohol, polyacrylamides, polyacrylic acid, poly(acrylonitrile-acrylic acid), polyurethanes, polyethylene glycol, polyethyleneoxide, poly(N-vinyl-2-pyrrolidone), polyacrylates such as poly(2-hydroxy ethyl methacrylate) and copolymers of acrylates with N-vinyl pyrrolidone, N-vinyl lactams, acrylamide, polyurethanes, other similar materials that form a hydrogel, and combinations thereof. The hydrogel materials further may be cross-linked to provide additional strength to the implant.

Additional components may be added to the polymer composition to further enhance its characteristics. In one embodiment, other elastomers are added to the polymer composition. Non-limiting examples of elastomers that may be added to the synthetic nucleus pulposus compositions include, but are not limited to, silicone, polyurethane, polybutadiene, silicone-polyurethane copolymers, polyolefins such as polyisobutylene and polyisoprene, neoprene, nitrile, vulcanized rubber, and combinations thereof.

When an elastomeric polymer is used in combination with a thermoplastic silicone polyurethane polymer, the elastomer may be added to the polymer blend in concentrations comprising, or alternatively consisting of, about 5-40% (by weight) of the total weight of the polymer composition.

In another preferred embodiment, polyelectrolytes can be used as the hydrophilic polymer, or are added in combination with the hydrophilic polymer to further enhance the hydrophilic nature of the synthetic spinal nucleus implant compositions. Non-limiting examples of polyelectrolytes that may be added to the spinal nucleus implant compositions include, but are not limited to, members of the following systems: proteins, nucleic acids, sulfonated styrene, and polyacrylic acids. Further examples include polymethacrylic acid, polystyrene sulfate, carboxymethylcellulose, xantham gum, pectins, polyallylamine hydrochloride, carrageenan, and combinations thereof. Polyelectrolytes are well known in the art, and one skilled in the art will appreciate still other examples of polyelectrolytes that may be used in the embodiments described herein.

Polyelectrolytes may be added to the polymer blend in concentrations comprising, or alternatively consisting of, about 5-100% (by weight) of the hydrophilic polymer, when used in combination with another hydrophilic polymer. The polyelectrolyte preferably is present in an amount ranging from about 5-25% (by weight), based on the weight of the hydrophilic polymer.

In an embodiment of the invention, the spinal nucleus implant composition comprises about 5% by weight of a polyacrylic acid as a first hydrophilic polymer, about 20% by weight polyvinyl alcohol as a second hydrophilic polymer, and about 75% by weight of a silicone polyurethane polymer as a non-hydrogel polymer material. Another preferred composition according to embodiments of the invention is a silicone polyurethane polymer as the non-hydrogel polymer material and a polyacrylic acid as the at least one hydrophilic polymer in a ratio of silicon polyurethane polymer to polyacrylic acid in the range of from about 19:1 to about 4:1, even more preferably from about 19:1 to about 4.5:1.

In another embodiment of the invention, the spinal nucleus implant may assume any appropriate geometry or size for implantation into the intervertebral disc space. For example, the spinal nucleus implant may be from about 3 mm to about 15 mm in height so as to accommodate a range of intervertebral disc space heights. The spinal nucleus implant also may range in volume from about 0.5 milliliters to about 10 milliliters so as to accommodate a range of intervertebral disc space volumes. One who is skilled in the art will appreciate the myriad geometries and sizes that the spinal nucleus implant may take, in accordance with the limitations herein.

Figure 2:
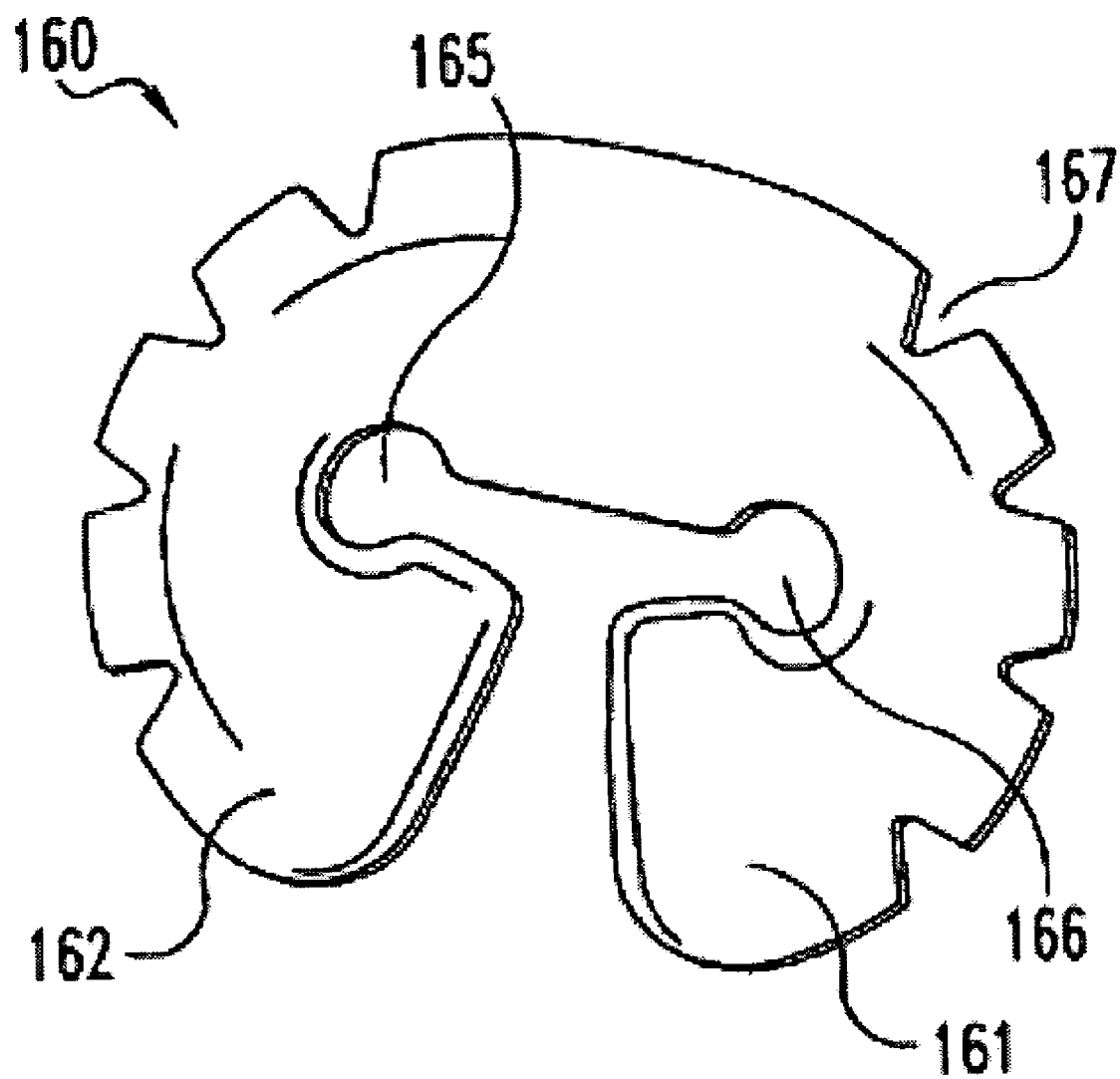
FIG. 2 shows the spinal nucleus implant of FIG. 1 in a partially straightened configuration.
Figure 3:
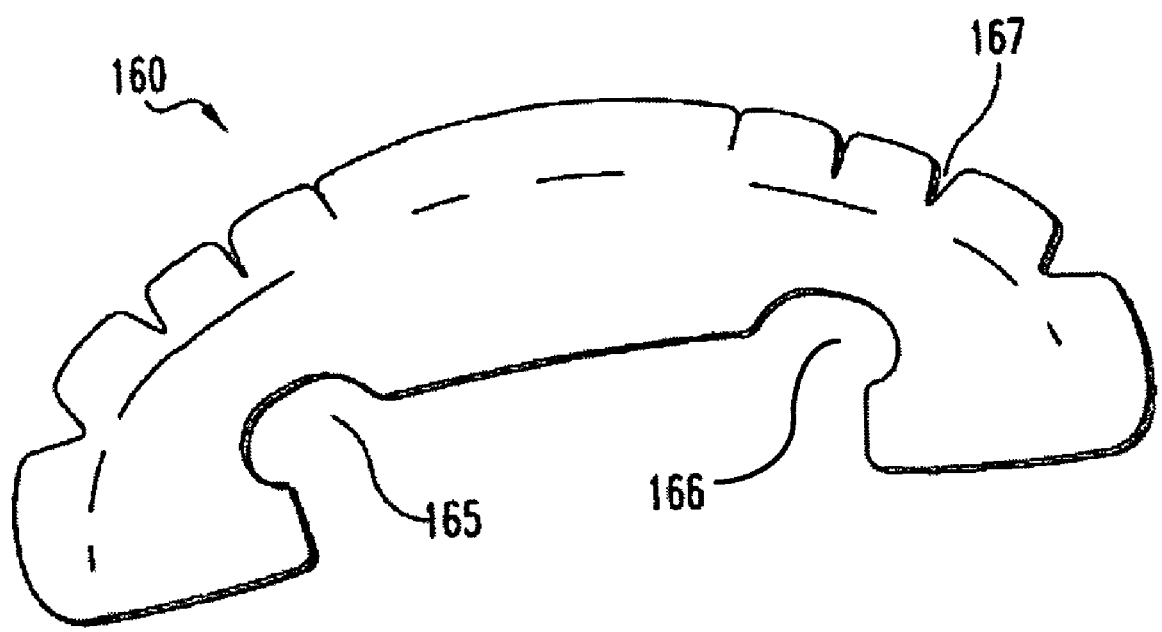
FIG. 3 shows the spinal nucleus implant of FIG. 1 in a nearly straightened configuration.

In another embodiment of the invention, the spinal nucleus implant comprises a plurality of implants, each with a hole passing therethrough. The implants have angled ends so that, when the implants are positioned within the annulus fibrosis and pulled together, a "C"-shaped implant is formed. In another embodiment, the implant is deformable such that the implant can be molded into an inherent shape, deformed into an insertion shape, or an indwelling shape following implantation, as shown in FIGS. 1-3, and described in more detail below. In a preferred embodiment, the implant is substantially deformable in the plane perpendicular to the spinal column but substantially less deformable in the direction parallel to the spinal column. In this way, the implant may be deformed into an insertion shape in the plane perpendicular to the spine but still provide adequate support to bear the vertical stresses imparted by the spine. The molded shape may be spherical, cylindrical, helixical, ovate, or any other appropriate shape.

The implant may have an angular, tapered shape similar to a three-dimensional trapezoid. Alternatively, the implant is molded into an elongated rod-like shape. Following implantation, the rod adapts into a spiral shape.

In another embodiment of the invention, the implant comprises, or alternatively consists of, a two-part implant that is joined together following insertion into the partially evacuated disc space.

Additionally, the nucleus implant described herein may be a component of a multi-part or multi-layer implant. For example, the nucleus implant may be the center of a nucleus implant surrounded by a fabric or another polymeric layer. The center of the multi-part implant may take any of the shapes discussed herein or any other appropriate shape for implantation. In another embodiment of the invention, the nucleus implant of the invention is the center layer of a three-layered nucleus implant. One possessing ordinary skill in the art, in light of known systems and methods, will appreciate the myriad implant configurations that may be produced.

The spinal nucleus implants further may comprise therapeutics, such as pharmacological agents and biological agents. Examples of pharmacological agents or biological agents include, but are not limited to, antibiotics, analgesics, anti-inflammatory drugs, steroids, anti-viral and anti-retroviral compounds, therapeutic proteins or peptides, and therapeutic nucleic acids (as naked plasmid or a component of an integrating or non-integrating gene therapy vector system).

Antibiotics useful with the spinal nucleus implants include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin. In addition, one skilled in the art of implant surgery or administrators of locations in which implant surgery occurs may prefer the introduction of one or more of the above-recited antibiotics to account for nosocomial infections or other factors specific to the location where the surgery is conducted. Accordingly, the invention further contemplates that one or more of the antibiotics recited supra, and any combination of one or more of the same antibiotics, may be included in the spinal nucleus implants of the invention.

The invention further contemplates that immunosuppresives may be administered with the spinal nucleus implants. Suitable immunosuppressive agents that may be administered in combination with the spinal nucleus implants include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the spinal nucleus implants include, but are not limited to, prednisolone, methotrexate, thalidomide, methoxsalen, rapamycin, leflunomide, Bredinin™ (mizoribine), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcep™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus). Other drugs useful with the nucleus pulposus include anti-cytokines such as anti-tumor necrosis factor alpha (anti-TNF alpha), anti-interleukin 2 (anti-IL2), anti-IL4, anti-Il10, anti-IL18, etc.)

The invention also contemplates the use of therapeutic polynucleotides or polypeptides (hereinafter "therapeutics") with the spinal nucleus implants of the invention. As noted supra, the therapeutics may be administered as proteins or peptides, or therapeutic nucleic acids, and may be administered as full length proteins, mature forms thereof or domains thereof, as well as the polynucleotides encoding the same. Examples of therapeutic polypeptides include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3; and Platelet Derived Growth Factors (PDGFs), including PDGF-A, PDGF-B, PDGF-C, and PDGF-D. The polynucleotides encoding the same also may be administered as gene therapy agents.

In a particularly preferred embodiment of the invention, the spinal nucleus implant comprises antagonists to either the myelin-associated glycoprotein (MAG) or Nogo-A, the largest transcript of the recently identified nogo gene (formerly called NI-220), which are both present in CNS myelin and have been characterized as potent inhibitors of axonal growth. For example, Nogo-A acts as a potent neurite growth inhibitor in vitro and represses axonal regeneration and structural plasticity in the adult mammalian CNS in vivo. In another embodiment of the invention, antagonists to both MAG and Nogo-A are co-administered to the patient. In this preferred embodiment of the invention, the spinal nucleus implants of the invention are used as implants for intervertebral discs that are adjacent locations of spinal cord injury, and may also replace damaged or infected native nucleus pulposus. In this embodiment of the invention, the inhibitory activity of the antagonist(s) to the activity of MAG and Nogo-A may aid in the regeneration of damaged spinal nerve tissue, and the spinal nucleus implant serves as a local reservoir of therapeutic antagonist(s) to aid in the growth of damaged spinal tissue. Antagonists of MAG and Nogo-A may take the form of monoclonal antibodies, anti-sense molecules, small molecule antagonists, and any other forms of protein antagonists known to those of skill in the art.

In this embodiment, therapeutic polypeptides or polynucleotides of Ninjurin-1 and Ninjurin-2 may further be administered alone or in conjunction with one or more MAG or Nogo-A antagonists, as a component of the spinal nucleus implant. Ninjurin-1 and Ninjurin-2 are believed to promote neurite outgrowth from primary cultured dorsal root ganglion neurons. Ninjurin-1 is a gene that is up-regulated after nerve injury both in dorsal root ganglion (DRG) neurons and in Schwann cells. The full-length proteins, mature forms or domains of the full-length proteins thereof may be administered as therapeutics, as well as the polynucleotides encoding the same.

The invention further contemplates a method of treating spinal cord injury using the spinal nucleus implants of the invention as a reservoir for therapeutic agents that promote the growth of injured spinal cord tissue or damaged nerves. The method includes administering at least one or more, including all, of the above-recited therapeutics as a component of the spinal nucleus implant of the invention. In one embodiment of the invention, the spinal nucleus implant material includes the therapeutic agents admixed with the implant compositions. In another embodiment of the invention, the therapeutic agents are applied to the spinal nucleus implant during the partial hydration step, prior to implantation of the nucleus pulposus. The therapeutic agents may be administered to the nucleus pulposus in any number of suitable fluids, such as for example, water and saline solution.

The spinal nucleus implants preferably are mixtures or blends of non-hydrogel polymer materials and at least one hydrophilic polymer, and can be produced using techniques known in the art. For example, the hydrophilic polymer may be melted and the non-hydrogel polymer material may be added thereto in an extruder, a blender, a mixer, a container, or a mold. Conversely, the non-hydrogel polymer material may be melted and the hydrophilic polymer added thereto in an extruder, a blender, a mixer, a container, or a mold. In another example, the non-hydrogel polymer can be melt fabricated by conventional injection molding, transfer molding, compression molding, reaction-injection molding, blow molding, insert molding, or extrusion molding techniques. Hydrophilic polymers may be added to the melted composition, and preferably are mixed to a nearly confluent blend, prior to introduction to a mold setting. Conversely, the hydrophilic polymers may be melt fabricated and the non-hydrogel polymer added to the melted composition prior to mold setting. Molds may be made of a metal such as aluminum, steel, iron, and mixtures thereof, or alternatively could be made of a ceramic. The size of the implant mold can be determined for each individual patient prior to production of the implant. Alternatively, the non-hydrogel/hydrophilic polymer mixture may be molded manually or automatically into a desired shape, and allowed to cure. Upon curing, the substantially solid molded material preferably is removed from the mold (if a mold us used) and optionally further processed (e.g., removing mold burrs, polished, etc.) to form the spinal nucleus implant.

Any non-hydrogel polymer and hydrophilic (or optionally polyelectrolyte) particle size suitable for forming a spinal nucleus implant can be used in the present invention. Preferably, the non-hydrogel polymer particles have a size prior to forming the mixture, within the range of from about 10 microns to about 10 mm, and the hydrophilic materials have a particle size prior to forming the mixture within the range of from about 10 microns to about 10 mm.

Methods of obtaining or producing non-hydrogel polymer materials and hydrophilic polymers is within the skill of a person having ordinary skill in the art, and techniques for the production of these compounds are available in the patent and scientific literature. Accordingly, using the guidelines provided herein, skilled artisans are capable of forming a suitable spinal nucleus implant composition including at least a non-hydrogel polymer material and at least one hydrophilic material.

Methods of producing therapeutic polynucleotides and polypeptides that may be co-administered with the spinal nucleus implants are well known to one of skill in the art. The present invention contemplates vectors containing the therapeutic polynucleotides recited supra, host cells, and the production of therapeutic polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. Useful vectors include, but are not limited to, plasmids, bacteriophage, insect and animal cell vectors, retroviruses, cosmids, and other single and double-stranded viruses.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination; origin of replication sequence, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The expression construct may further contain sequences such as enhancer sequences, efficient RNA processing signals such as splicing and polyadenylation signals, sequences that enhance translation efficiency, and sequences that enhance protein secretion.

Expression systems and methods of producing therapeutics, such as recombinant proteins or protein fragments, are well known in the art. For example, methods of producing recombinant proteins or fragments thereof using bacterial, insect or mammalian expression systems are well known in the art. (See, e.g., Molecular Biotechnology: Principles and Applications of Recombinant DNA, B. R. Glick and J. Pasternak, and M. M. Bendig, Genetic Engineering, 7, pp. 91-127 (1988), for a discussion of recombinant protein production).

The expression vectors preferably will include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate host cells for expression include, but are not limited to, bacterial cells, such as *E. coli, Streptomyces* and *Salmonella typhimurium* cells; fungal cells, such as *Pichia, Saccharomyces* and other yeast cells; insect cells such as *Drosophila* S2 and *Spodoptera* Sf9 and Sf21 cells; animal cells such as CHO, COS, 293, and Bowes melanoma cells; and plant cells. Appropriate culture mediums and conditions for the above-described host cells are known in the art.

Examples of vectors for use in prokaryotes include pQE30Xa and other pQE vectors available as components in pQE expression systems available from QIAGEN, Inc. (Valencia, Calif.); pBluescript vectors, Phagescript vectors, pNH8A, pNH16a, pNH18A, pNH46A, available from Stratagene Cloning Systems, Inc. (La Jolla, Calif.); and Champion™, T7, and pBAD vectors available from Invitrogen (Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

A polypeptide of an embodiment of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

In another embodiment of the invention, therapeutic agents can be produced using bacterial lysates in cell-free expression systems that are well known in the art. Commercially available examples of cell-free protein synthesis systems include the EasyXpress System from Qiagen, Inc. (Valencia, Calif.).

Therapeutics also can be recovered from the following: products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, therapeutics may be glycosylated or may be non-glycosylated. In addition, therapeutics may also include an initial modified methionine residue, in some cases as a result of host-mediated processes. Thus, it is known that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Therapeutics also may be isolated from natural sources of polypeptide. Therapeutics may be purified from tissue sources, preferably mammalian tissue sources, using conventional physical, immunological and chemical separation techniques known to those of skill in the art. Appropriate tissue sources for the desired therapeutics, or other techniques for obtaining the recited therapeutics such as PCR techniques, are known or are available to those of skill in the art.

The invention also encompasses methods of treating spinal injury in which the nucleus pulposus contributes to the development of the disease, such as for example a herniated disc, by replacing at least a portion of the native nucleus pulposus material.

In one embodiment of the invention, the dysfunctional intervertebral disc is accessed surgically and at least a portion of the native nucleus pulposus material and any free disc fragments are removed. Subsequently, the synthetic nucleus implant is delivered to the at least partially evacuated disc space. Delivery of the synthetic nucleus implant to the at least partially evacuated disc space may be achieved, for example, using minimally invasive surgical techniques and devices. Therefore, synthetic nucleus implant may be delivered via a cannula to the at least partially evacuated disc space. Alternatively, the synthetic nucleus implant may be delivered to the at least partially evacuated disc space in a more direct manner absent a cannula. The appropriate delivery method is selected by a surgeon skilled in the art of intervertebral disc repair and replacement.

In one embodiment of the invention, the polymer compositions are useful in the replacement of native nucleus pulposus materials. In another embodiment, the polymer compositions are useful in the prevention or treatment, or for aiding in the prevention or treatment, of diseases and/or disorders associated with the spinal column. Non-limiting examples of diseases and/or disorders that the polymer compositions of the embodiments are useful in preventing or treating include, but are not limited to: bulging disc(s); herniated disc(s); spinal injury due to trauma; age-related degeneration or failure of spinal column components (namely intervertebral disc(s)); spinal instability; discogenic back pain; intervertebral osteochondrosis; spondylolisthesis; spinal infection; spinal tumors; and arthritis of the spine.

The polymer compositions preferably are administered to the patient in substantially dehydrated form, and absorb water and swell after administration to the patient. Following hydration of the polymer compositions of the invention, the hydrated polymer compositions substantially fill the at least partially evacuated cavity of the disc space. In another embodiment of the invention, the spinal nucleus implant is partially hydrated prior to implantation in the patient. Appropriate hydrating fluids include, but are not limited to, water, saline solution, and calcium-phosphate based solutions. A suitable method of delivering or implanting the spinal nucleus implant device of the invention is described in, for example, U.S. Patent Application Publication No. 2004/0117019 (application Ser. No. 10/717,687), the disclosure of which is incorporated by reference herein in its entirety.

The size of the spinal nucleus implant device, when fully hydrated, can be varied for different individuals. A typical size of an adult intervertebral disc is 2 cm in the semi-minor axis, 4 cm in the semi-major axis and 1.2 cm in thickness. The embodiments contemplate numerous sizes for the spinal nucleus implant to accommodate different sizes of individual patients, relative to the typical size set forth above. Using the guidelines provided herein, skilled artisans are capable of determining an appropriately sized spinal nucleus implant, depending on the size and age of the patient, as well as on the amount of disc material removed or evacuated from the disc space.

The spinal nucleus implant described in the embodiments preferably occupies at least 50% of the evacuated intervertebral disc space, more preferably 70% of the evacuated intervertebral disc space, even more preferably 80% of the intervertebral disc space, even more preferably 90% of the evacuated intervertebral disc space, and most preferably 99% or more of the evacuated intervertebral disc space. The appropriate size of the implant can be determined for a particular patient by measuring the volume of the evacuated disc space with an injectable saline balloon, or by other techniques known to those skilled in the art.

In an additional embodiment, the spinal nucleus implants are packaged in kits under sterile conditions prior to implantation into a patient. The spinal nucleus implant may be included as a component of a surgical kit for implanting the device, along with other surgical tools or instruments. Preferably, the kit comprises the spinal nucleus implant together with a minimally invasive delivery apparatus.

A preferred delivery apparatus includes a cannula adapted to both contain and position the spinal nucleus implant in a minimally invasive fashion. The dimensions of the cannula are selected according to the specific features of the tissue site. Accordingly, the longitudinal dimension, curvature, width or circumference of the cannula can vary. The delivery apparatus can further comprise a placement feature for use in positioning the implant. The placement tool can include an elongated rod having a plate or other device for positioning the implant, adapted to be movably contained within the cannula. The movement of the elongated rod is controlled by the surgeon and can be in the form of a syringe-like structure, a trigger, and the like. Accordingly, when pushed forward, the placement tool expels or ejects the spinal nucleus implant from the distal end of the cannula into the evacuated annulus fibrosis. A suitable delivery device is disclosed in U.S. Patent Application Publication No. 2004/0117019 (application Ser. No. 10/717,687), the disclosure of which is incorporated by reference herein in its entirety.

FIGS. 1-3 illustrate one preferred embodiment of a spinal nucleus implant that may be implanted with a disc delivery instrument. Spinal nucleus implant 160 preferably is molded into a "C" configuration, and comprises a pair of arms 161 and 162 that are folded to form an inner fold 163 when the implant is in its relaxed configuration. The folded arms abut one another at their ends 161a and 162a when the implant is relaxed, so that the center core 164 of the implant (when viewed from above as in FIG. 1) is substantially solid.

Apertures 165 and 166 can be included to correspond to posts present on a disc delivery instrument (not shown) similar to that described in U.S. Patent Application Publication No. 2004/0117019. When the posts are inserted into the apertures and the hinged channel members are pivoted to an angle of about 180°, implant 160 straightens to provide a cross sectional size that is less than the cross sectional size of the folded implant (compare FIG. 3 to FIG. 1). Grooves 167 are provided on the outer surface to prevent cracking or tearing of the implant when the implant is in its straightened configuration. X-ray markers such as tantalum markers 168 may be included to assist in positioning the implant. Preferably, a larger x-ray marker is provided in the anterior portion of the implant, and smaller x-ray markers are provided in posterior portions of the implant.

Figure 4:
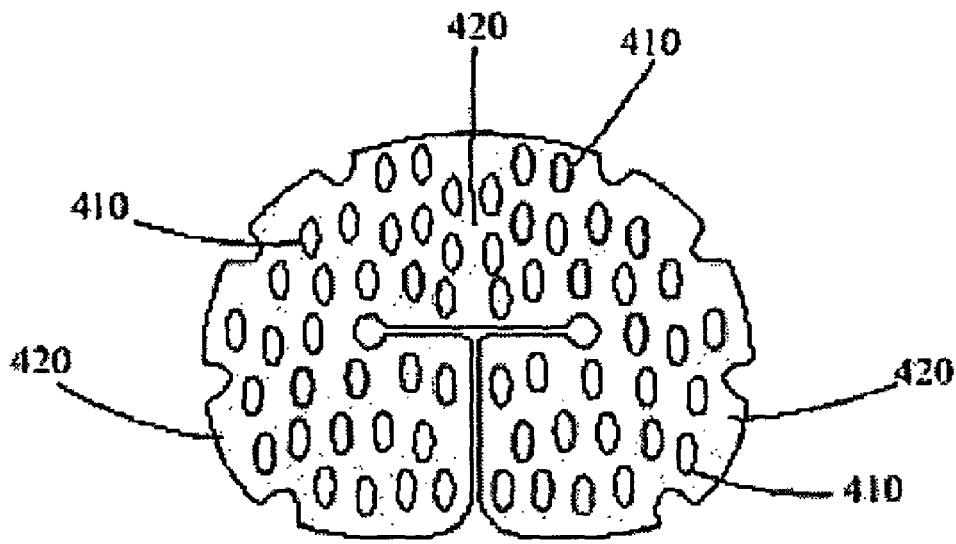
FIG. 4 shows the spinal nucleus implant of FIG. 1 as a heterogeneous composite.
Figure 5:
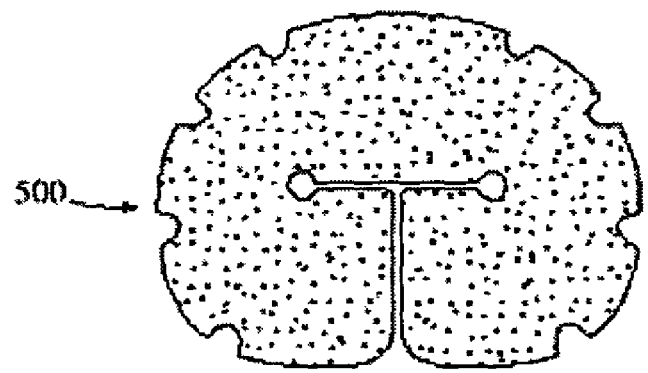
FIG. 5 shows the spinal nucleus implant of FIG. 1 as a homogeneous composite.

FIGS. 4-5 illustrate two preferred embodiments of the present invention. FIG. 4 illustrates a heterogeneous composite spinal nucleus implant wherein the non-hydrogel polymer material 420 and the at least one hydrophilic polymer 410 have been heterogeneously mixed and cast, molded, or otherwise shaped into a spinal nucleus implant. Though the particles of the at least one hydrophilic polymer 410 are depicted as small cylindrically-shaped particles, it is to be understood that the particles could be any shape such as spherical beads, microspheres, granules, powder, fine powder, course powder, flakes, fibrous, elongated, irregularly shaped, etc. FIG. 5 illustrates a homogenous composite material where the non-hydrogel polymer material and the at least one hydrophilic polymer have been mixed into a homogenous composite 500. Accordingly, the at least one hydrophilic polymer is depicted as black dots against the background of the non-hydrogel polymer material.

The invention may be practiced in ways other than those particularly described in the foregoing description and examples. Numerous modifications and variations of the invention are possible in light of the above teachings and, therefore, are within the scope of the appended claims.

The entire disclosure of each document cited (including patents, patent applications, journal articles, abstracts, manuals, books, or other disclosures) in the Background of the Invention, Detailed Description, and Examples is herein incorporated by reference in their entireties.

EXAMPLES

I. Production of a Spinal Nucleus Implant

A thermoplastic silicone polyurethane is obtained and used to create a spinal nucleus implant. The thermoplastic silicone polyurethane compound is admixed with polyacrylic acid in a 4 to 1 ratio, and the mixture is processed through an injection molding process into a spinal nucleus implant approximating the implant illustrated in FIGS. 1-3. The completed mold spinal nucleus implant is maintained and packaged under sterile conditions into sterile packaging in a substantially dehydrated form, and is provided for implantation to surgeons.

II. Implantation of a Spinal Nucleus Implant

A patient suffering from a herniated disc undergoes corrective surgery, which includes removal of at least a portion of the native nucleus pulposus material along with any free disc fragments from the annulus fibrosis. The appropriate size of the implant is determined for the patient by measuring the volume of the evacuated disc space with an injectable saline balloon. A spinal nucleus implant is produced that, when fully hydrated, occupies up to at least about 99% of the evacuated disc space.

The spinal nucleus implant is introduced into the evacuated disc space using delivery devices well known in the art, for example, those delivery devices described in U.S. Pat. Nos. 5,800,549 and 5,716,416, and in U.S. Patent Application Publication No. 2004/0117019. The spinal nucleus implant may optionally be partially hydrated prior to delivery of the implant to the evacuated annulus fibrosis. The spinal nucleus implant is coated with at least one appropriate antibiotic prior to implantation in the patient. Following implantation, the annulus fibrosis can be surgically closed.

The patient recovers after surgery, allowing the spinal nucleus implant to achieve complete hydration. If necessary, the stability of the spinal nucleus implant is evaluated using Magnetic Resonance Imaging (MRI) analysis.

The invention has been described with reference to particularly preferred embodiments and examples. Those skilled in the art will appreciate that various modifications may be made to the invention without departing from the spirit and scope thereof.

What is claimed is:

1. A spinal nucleus implant comprising a heterogeneous mixture of non-hydrogel polymer material and at least one hydrophilic polymer wherein the non-hydrogel polymer material and the at least one hydrophilic polymer are present in a weight ratio from about 1:1 to about 19:1, wherein the implant has a tapered cross-section formed by the ratio of non-hydrogel polymer material to hydrophilic polymer in the posterior side of the implant from about 19:1 to about 10:1 and in the anterior side from about 10:1 to about 1:1, and wherein, upon hydration, said implant occupies at least 50% of evacuated disc space.

2. The spinal nucleus implant of claim 1, wherein the implant has a shape selected from the group consisting of a substantially "C"-shape, spherical, cylindrical, helixical, ovate, tapered three-dimensional trapezoid, or rod-like shape.

3. The spinal nucleus implant of claim 1, wherein the implant has a height within the range of from about 3 mm to about 15 mm.

4. The spinal nucleus implant of claim 1, wherein the implant has a volume within the range of from about 0.5 mL to about 10 mL.

5. The spinal nucleus implant of claim 1, wherein the implant is substantially deformable in the plane perpendicular to the spine and substantially less deformable in the direction parallel to the spine.

6. The spinal implant of claim 1, wherein the non-hydrogel polymer and the at least one hydrophilic polymer are present in a weight ratio from about 3:1 to about 19:1.

7. The spinal implant of claim 1, wherein the non-hydrogel polymer and the at least one hydrophilic polymer are present in a weight ratio from about 4.5:1 to about 19:1.

8. A method of making a spinal nucleus implant comprising: mixing a non-hydrogel polymer material and at least one hydrophilic polymer to form a heterogeneous or homogeneous mixture, wherein the non-hydrogel polymer material and the at least one hydrophilic polymer are present in a weight ratio from about 1:1 to about 19:1; molding the mixture into a nucleus implant wherein the implant has a tapered cross-section formed by the ratio of non-hydrogel polymer material to hydrophilic polymer in the posterior side of the implant from about 19:1 to about 10:1 and in the anterior side from about 10:1 to about 1:1; and curing or solidifying the non-hydrogel polymer to form the spinal nucleus implant.

9. The method of claim 8, wherein molding comprises injection molding, transfer molding, compression molding, reaction-injection molding, blow molding, insert molding, or extrusion molding.

10. The method of claim 8, wherein mixing comprises melting the non-hydrogel polymer material and adding the hydrophilic material to the molten non-hydrogel polymer material in an extruder, a blender, a mixer, a container, or a mold.

11. The method of claim 8, wherein mixing comprises melting the hydrophilic material and adding the non-hydrogel polymer material to the molten hydrophilic material in an extruder, a blender, a mixer, a container, or a mold.

12. The method of claim 8, wherein the non-hydrogel polymer and the at least one hydrophilic polymer are present in a weight ratio from about 3:1 to about 19:1.

13. The spinal implant of claim 1, wherein the non-hydrogel polymer and the at least one hydrophilic polymer are present in a weight ratio from about 4.5:1 to about 7:1.

14. A method of treating or preventing a disease or disorder associated with the spine, comprising: surgically evacuating at least a portion of the nucleus pulposus material and any free disc fragments from an intervertebral disc space; producing a spinal nucleus implant as claimed in claim 8; and implanting the spinal nucleus implant into the at least partially evacuated intervertebral disc space.

15. The method of claim 14, further comprising measuring the volume of the at least partially evacuated intervertebral disc space by an injectable balloon prior to implanting the spinal nucleus implant.

16. The method of claim 14, wherein the disease or disorder is selected from the group consisting of: bulging disc(s); herniated disc(s); spinal injury due to trauma; age-related degeneration or failure of spinal column components; spinal instability; discogenic back pain; intervertebral osteochondrosis; spondylolisthesis; spinal infection; spinal tumors; arthritis of the spine; and combinations thereof.

* * * * *

UNITED STATES PATENT AND TRADEMARK OFFICE
CERTIFICATE OF CORRECTION

PATENT NO. : 7,857,856 B2
APPLICATION NO. : 11/079773
DATED : December 28, 2010
INVENTOR(S) : Trieu It is certified that error appears in the above-identified patent and that said Letters Patent is hereby corrected as shown below:

On the Face Page, in Field (73), under "Assignee", in Column 1, Line 1, delete "Ortho Pedic, Inc." and insert -- Orthopedic, Inc. (US) --, therefor.

In Column 6, Line 15, delete "xantham" and insert -- xanthan --, therefor.

In Column 7, Line 61, delete "Cellcep™" and insert -- Cellcept™ --, therefor.

In Column 7, Line 61, delete "motefil," and insert -- mofetil --, therefor.

In Column 8, Line 2, delete "(anti-IL2)," and insert -- (anti-IL2, --, therefor.

In Column 14, Line 56, in Claim 6, delete "spinal" and insert -- spinal nucleus --, therefor.

In Column 14, Line 59, in Claim 7, delete "spinal" and insert -- spinal nucleus --, therefor.

In Column 16, Line 1, in Claim 13, delete "spinal" and insert -- spinal nucleus --, therefor.

Signed and Sealed this
Fourth Day of October, 2011

David J. Kappos
*Director of the United States Patent and Trademark Office*